(12) United States Patent
Sauter et al.

(10) Patent No.: US 12,102,493 B2
(45) Date of Patent: Oct. 1, 2024

(54) DENTAL OR SURGICAL HANDPIECE WITH AN RFID TRANSPONDER

(71) Applicant: KAVO DENTAL GMBH, Biberach (DE)

(72) Inventors: Johannes Sauter, Mittelbuch (DE); Johann Stempfle, Pfaffenhofen (DE)

(73) Assignee: KAVO DENTAL GMBH, Biberach (DE)

( * ) Notice: Subject to any disclaimer, the term of this patent is extended or adjusted under 35 U.S.C. 154(b) by 683 days.

(21) Appl. No.: 17/279,956

(22) PCT Filed: Sep. 25, 2019

(86) PCT No.: PCT/EP2019/075785
§ 371 (c)(1),
(2) Date: Mar. 25, 2021

(87) PCT Pub. No.: WO2020/064789
PCT Pub. Date: Apr. 2, 2020

(65) Prior Publication Data
US 2021/0386509 A1   Dec. 16, 2021

(30) Foreign Application Priority Data
Sep. 26, 2018  (DE) ...................... 10 2018 123 694.8

(51) Int. Cl.
*A61B 90/98* (2016.01)
*A61C 1/12* (2006.01)
*A61C 1/14* (2006.01)

(52) U.S. Cl.
CPC ................ *A61B 90/98* (2016.02); *A61C 1/12* (2013.01); *A61C 1/141* (2013.01); *A61C 2204/005* (2013.01)

(58) Field of Classification Search
CPC ........... A61B 90/98; A61C 1/12; A61C 1/141; A61C 2204/005; G06K 19/0723; H04B 10/50; H04B 10/60
See application file for complete search history.

(56) References Cited

U.S. PATENT DOCUMENTS

| 2007/0065774 A1* | 3/2007 | Pernot | A61C 1/12 |
| | | | 433/133 |
| 2016/0074134 A1* | 3/2016 | Kuhn | A61C 1/0061 |
| | | | 433/114 |

(Continued)

FOREIGN PATENT DOCUMENTS

| DE | 102010011630 A1 | 9/2011 |
| EP | 0233103 A1 | 8/1987 |

(Continued)

OTHER PUBLICATIONS

International Search Report with Written Opinion for related Application No. PCT/EP2019/075785 dated Dec. 12, 2019 (14 Pages).

*Primary Examiner* — Jan Christopher L Merene
*Assistant Examiner* — Luis Ruiz Martin
(74) *Attorney, Agent, or Firm* — Michael Best & Friedrich LLP

(57) ABSTRACT

The invention provides for a dental or surgical handpiece with an elongated handle sleeve (110) and a head piece (50) attached to the front end of the handle sleeve (110) that serves to to detachably receive a dental tool as well as for a clamping mechanism (20) formed in the head piece (50) to detachably hold the tool, the clamping mechanism (20) having a push-button (10) for actuating the clamping mechanism (20). The handpiece further has an RFID transponder (5) for identifying the handpiece. The push-button (10) consists of a heat-insulating electrically non-conductive plastic or m ceramic material with a plate-shaped recess that holds the RFID transponder (5). The push-button (10) has a (Continued)

flat round shape so that the RFID transponder (5), because of the equally flat round shape of its coil, can be integrated very well into it. Particularly advantageous ambient electrical conditions can be achieved for the RFID transponder as the push-button (10) is made of an electrically non-conductive material. An advantageous thermal insulation is provided as the push-button (10) is made of a heat-insulating material.

18 Claims, 2 Drawing Sheets

(56) References Cited

U.S. PATENT DOCUMENTS

2016/0262847 A1* 9/2016 Rickert ............... A61C 1/12
2021/0298872 A1* 9/2021 Pfleiderer ........... A61C 1/08

FOREIGN PATENT DOCUMENTS

| EP | 2581061 A1 | 4/2013 |
|----|------------|--------|
| EP | 3067008 A1 | 9/2016 |

* cited by examiner

DENTAL OR SURGICAL HANDPIECE WITH AN RFID TRANSPONDER

BACKGROUND OF THE INVENTION

The invention relates to a dental or surgical handpiece with an RFID transponder (RFID: radio-frequency identification).

It is common medical practice to document the use of aids and devices. This also applies to the treatment and hygiene condition (e.g. sterility) of aids or devices. To this end, relevant entries are predominantly made manually or are entered in a practice management program. There are systems in use where a data matrix code attached to the respective instrument is recorded with a scanner, so that a corresponding manual entry is unnecessary and thus avoiding the risk of transmission errors.

The methods currently in use require the code or identifier to be scanned or entered manually for registration. A transmission of information about the relevant instrument, e.g. regarding its hygiene condition or the number of uses is here not possible.

From EP 3 067 008 B1 a dental handpiece with an RFID transponder integrated in its handle is known. The manufacture of this handpiece requires leaving out a piece from the metal handle, placing the RFID transponder in that recess and then covering the recess with a plastic material so that data can be read out in environments unfavourable for radio transmissions (e.g. metal). Thus the manufacture involves considerable effort.

Additionally, the handpiece known from EP 3 067 008 B1 can hardly be obtained by "retrofitting" a handpiece that is not equipped with an RFID transponder.

Furthermore, DE 10 2010 011 630 A1 discloses a dental or surgical handpiece with an elongated handle sleeve and a head piece attached to the front end of the handle sleeve to detachably receive a dental tool. A clamping mechanism formed in the head piece to detachably hold the tool is equipped with a push-button, the bottom area of which is provided with a recess. This latter serves to enable the engagement of a spring, whereby the installation height of the head area can be reduced.

SUMMARY OF THE INVENTION

The invention is based on the objective of specifying a corresponding improved handpiece. In particular, the handpiece should be able to provide advantages concerning its manufacturing options and its electrical properties. In addition, a corresponding head piece should be specified for such a handpiece.

This objective is achieved according to the invention with the items mentioned in the independent claims. Particular embodiments of the invention are specified in the dependent claims.

According to the invention, a dental or surgical handpiece is provided, with an elongated handle sleeve and a head piece attached to the front end of the handle sleeve, which serves to detachably receive a dental tool and a clamping mechanism formed in the head piece to detachably hold the tool, the clamping mechanism having a push-button for actuating the clamping mechanism. The handpiece further has an RFID transponder for identifying the handpiece. The push-button consists of a heat-insulating electrically non-conductive plastic or ceramic material with a plate-shaped recess that holds the RFID transponder.

The push-button has a flat round shape, so that the RFID transponder can be very well integrated into the push-button because of the equally round flat shape of its coil. Nevertheless, the RFID transponder is arranged such that it is well protected against mechanical influences.

As the push-button is made of an electrically non-conductive material, particularly advantageous ambient electrical conditions can be achieved for the RFID transponder, in particular an "air gap" can thus be favourably realized for the RFID transponder or a suitable distance to metal components of the handpiece. The push-button is located at an exposed point of the handpiece, further providing particularly good reception conditions.

Thermal insulation is provided through the fact that the push-button is made of a heat-insulating material. This reduces the risk of the push-button heating up undesirably e.g. through a rotation of the tool and thus burning either a user of the handpiece or a patient.

In addition, the push-button is a component that is designed independently of a handle or handle sleeve of the handpiece. Thus it is possible to simply "retrofit" a corresponding handpiece that has a push-button without an RFID transponder, by replacing the push-button with an RFID-transponder corresponding to the application.

The RFID transponder arranged in the recess is preferably potted with a potting compound. This is advantageous in terms of manufacturing and also provides particularly good ambient electrical conditions for the RFID transponder.

The RFID transponder is preferably at a distance from a bottom surface of the plate-shaped recess, the space between the RFID transponder and the bottom surface being filled by the potting compound. This way it can be achieved to have a gap between the antenna of the RFID transponder and a metal base so that the fieldlines lines can easily flow through the antenna.

The potting compound that fills the plate-shaped recess and surrounds the RFID transponder preferably forms a region that is raised compared to the surface region surrounding the push-button, whereby the recess and the raised area preferably have an approximately circular outer contour. This is advantageous with regard to the ambient electrical conditions of the antenna of the RFID transponder. In addition the maximum protrusion of the potting compound relative to the surrounding surface region of the push-button is preferably smaller than 2 mm, preferably it is 1 mm to 2 mm.

In addition, preferably the protruding potting compound essentially extends the surface region surrounding the push-button continuously in an ergonomically advantageous manner.

Preferably, the push-button is arranged at an upper side of the head piece opposite the tool, whereby the plate-shaped recess is preferably essentially formed at the centre of the push-button. In this way, the push-button can be designed to be particularly suitable for actuating the clamping mechanism.

The plastic is preferably polyetheretherketone (PEEK); this material can be sterilized repeatedly. The potting compound preferably contains resin and/or silicone.

The handle sleeve and the head piece are preferably made in a user-friendly way out of a metal. The handle sleeve is preferably angled to be easy to handle.

The handpiece is particularly suitable if it contains, in the handle sleeve, a drive motor or a shaft that is coupled to an external drive motor, the handle sleeve further housing a bearing-mounted drive train for transmitting a rotational motion to the tool held at the headpiece. The clamping mechanism preferably has a collet for holding a shaft of the tool.

According to a further aspect of the invention, a head piece is provided for a dental or surgical handpiece, the head piece serving to detachably receive a dental tool. A clamping mechanism is formed in the head piece for detachably holding the tool, said clamping mechanism having a push-button for actuating the clamping mechanism. The push-button consists of a heat-insulating electrically non-conductive plastic or ceramic material with a plate-shaped recess that holds a RFID transponder intended for identifying the handpiece.

BRIEF DESCRIPTION OF THE DRAWINGS

The invention is explained in more detail below using a design example and with reference to the figures. The figures show the following.

DETAILED DESCRIPTION

Figure 1:
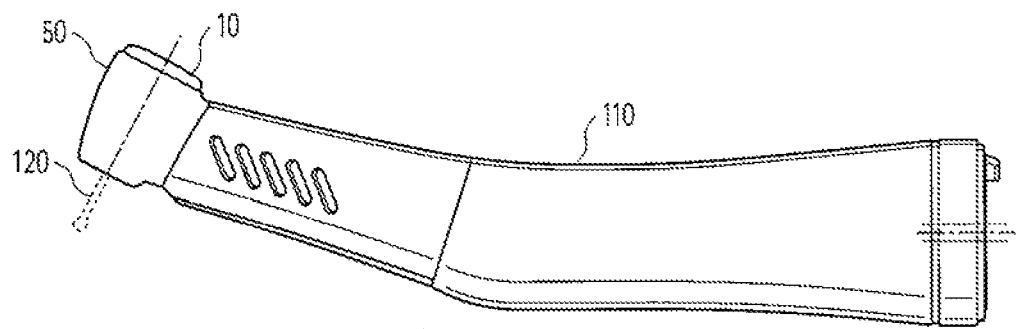
FIG. 1 a sketch of a handpiece corresponding to the application.

FIG. 1 shows a sketch of a lateral view of a dental or surgical handpiece 100 corresponding to the application. The handpiece 100 has an elongated handle sleeve 110. A head piece 50 for detachably receiving a dental tool 120 is preferably arranged at the front end of the handle sleeve 110. The handle sleeve 110 and the head piece 50 are preferably made of metal. As sketched as an example in FIG. 1, the handle sleeve 110 is preferably angled in an ergonomically advantageous manner.

The handpiece 100 may in particular be a so-called elbow piece or a so-called turbine.

Figure 2:
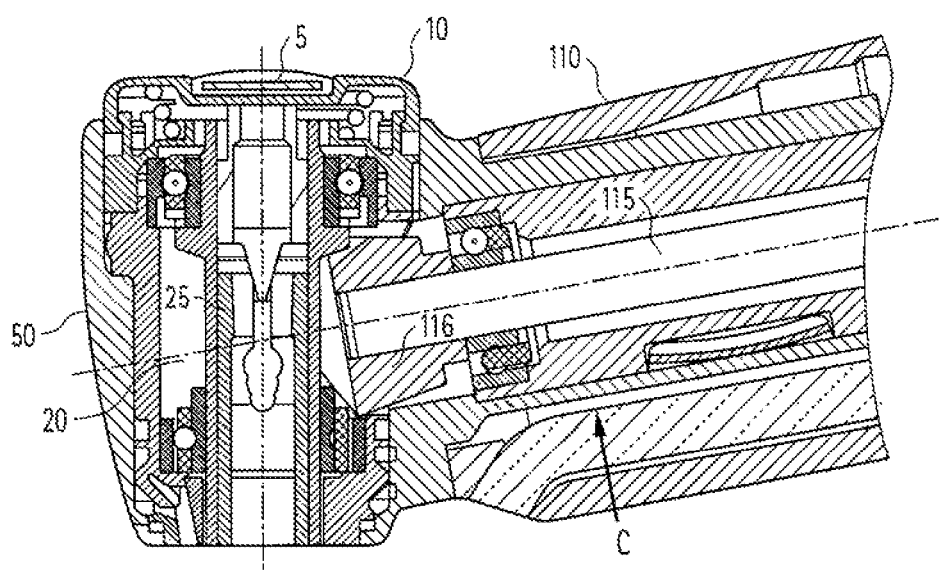
FIG. 2 a cross-sectional sketch through the head piece of the handpiece.
Figure 3:
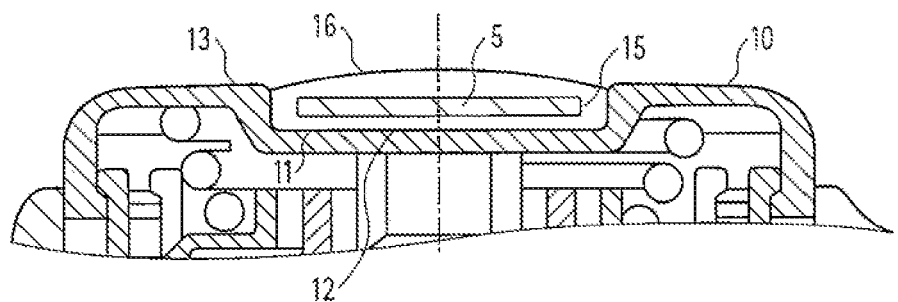
FIG. 3 an enlarged representation from FIG. 2 showing the area around the push-button.

FIG. 2 shows a cross-sectional sketch through the head piece 50. A clamping mechanism 20 is formed in the head piece 50 for detachably holding the tool 120, said clamping mechanism 20 having a push-button 10 for actuating the clamping mechanism 20. FIG. 3 shows the area around push-button 10 in more detail.

The handpiece 100 further has an RFID transponder 5 designed for identifying the handpiece 100.

The push-button 10 consists of a heat-insulating electrically non-conductive plastic or ceramic material. The plastic material may in particular be PEEK. If the push-button 10 is made of a ceramic material, information such as a logo or the like can be permanently applied, e.g. by means of a CO2 laser.

A plate-shaped recess 11 holding the RFID transponder 5 is arranged in or on the push-button 10. The RFID transponder 5 is potted with a potting compound 15, preferably containing resin and/or silicone.

As is the case in the example shown, the RFID transponder 5 is at a distance from the bottom surface 12 of the plate-shaped recess 11, the space between the RFID transponder 5 and the bottom surface 12 being filled by the potting compound 15.

If an RFID transponder is in general placed too close to a metal object, the field lines lines run into the metal and are not closed; this this case, no communication can take place between the RFID transponder 5 and a corresponding reception unit. Through the structure described here, it is possible to still have a gap between the antenna of the RFID transponder 5 and a metal surface corresponding to the application so that the field lines can flow through the antenna well, and can flow around the RFID transponder 5 in a closed shape. Thus advantageous ambient electrical conditions can be created for the RFID transponder 5.

An electrical memory contained in the RFID transponder 5 can be used, for example, to unambiguously identify the handpiece 100. Information about the hygiene status of the handpiece 100, a duration of use, a frequency of use, etc. can be stored in a read/write memory of the RFID transponder 5 or also in a memory of a central management system.

Information about the state of the handpiece 100 can thus be made to "attach" to the handpiece 100; this information can be updated when the handpiece 100 is used or treated and, if necessary, also transmitted to the central management system.

The potting compound 15 filling the plate-shaped recess 11 and surrounding the RFID transponder 5, preferably forms, as can be seen from FIG. 3, a raised area 16 relative to the surrounding surface region 13 of the push-button 10. The recess 11 and the raised area 16 preferably have an approximately circular outer contour. In principle, the RFID transponder 5 can be arranged such that it protrudes to a greater or lesser extent from the push-button 10. In this way, the distance to the bottom surface 12, i.e. the "gap width", can be adjusted. However, the RFID transponder 5 should not protrude too far, as the head piece 50 with the push-button 10 and the RFID transponder 5 would in that case in total reach a size that is fundamentally undesirable.

Thus the maximum protrusion of the potting compound 15 relative to the surrounding surface region 13 of the push-button 10 is preferably less than 2 mm and most preferably is 1 mm to 2 mm.

Furthermore the design is preferably such that the protruding potting compound 15 essentially continuously extends the surface region 13 surrounding the push-button 10.

Preferably the handle sleeve 110 in the handpiece 100 houses a drive motor or a shaft 115 that is coupled to an external drive motor, the handle sleeve 110 further housing a bearing-mounted drive train 116 for transmitting a rotational motion to the tool 120 held at the headpiece 50. The clamping mechanism 20 preferably has a collet 25 designed to hold a shaft of the tool 120.

As can be seen from FIG. 2, in the shown example, the push-button 10 is arranged at an upper side of the head piece 50 opposite the tool 120, the plate-shaped recess 11 preferably being formed essentially at the centre of the push-button 10. In particular, the push button 10 can be designed to actuate the collet 25.

The following features help improve the reading, writing, and distance conditions:

The antenna of the RFID transponder 5 has a small distance (air gap) to a metal environment.

The antenna of the RFID transponder 5 protrudes from the metal environment.

The antenna of the RFID transponder 5 is located on or in the push-button 10, which is made of an electrically non-conductive and non-magnetic material.

The push-button 10 is made of plastic or ceramic material.

The RFID transponder 5 is encased in plastic or ceramic material.

The production procedure may provide for a drop of the potting compound 15 to be placed on the bottom surface 12 of the recess 11 so that the drop forms the gap. Further potting compound is then added to pot the RFID transponder 5 on top, the drop not having dried yet and thus forming a uniform potting compound.

What is claimed is:

1. A dental or surgical handpiece with comprising:
   an elongated handle sleeve,
   a head piece arranged at the front end of the handle sleeve for detachably receiving a dental tool,
   a clamping mechanism formed in the head piece for detachably holding the tool, said clamping mechanism having a push-button for actuating the clamping mechanism, the push-button including a heat-insulating electrically non-conductive plastic or ceramic material with a plate-shaped recess, and
   an RFID transponder provided for identifying the handpiece, the RFID transponder being disposed in the plate-shaped recess of the push-button; wherein the plate-shaped recess is on top of the push-button and the plate-shaped recess opens away from the head piece.

2. The dental or surgical handpiece according to claim 1, wherein
   the RFID transponder arranged in the plate-shaped recess is potted with a potting compound.

3. The dental or surgical handpiece according to claim 2, wherein
   the RFID transponder is at a distance from the bottom surface of the plate-shaped recess, the space between the RFID transponder and the bottom surface being filled by the potting compound.

4. The dental or surgical handpiece according to claim 2, wherein
   the potting compound filling the plate-shaped recess and surrounding the RFID transponder forms a raised area relative to the surrounding surface area of the push-button, the recess and the raised area having an approximately circular outer contour.

5. The dental or surgical handpiece according to claim 4, wherein
   the maximum protrusion of the potting compound relative to the surrounding surface region of the push-button is smaller than 2 mm.

6. The dental or surgical handpiece according to claim 5, wherein
   the potting compound is configured to continuously extend over the surrounding surface area of the push-button.

7. The dental or surgical handpiece according to claim 2, wherein
   the potting compound contains resin and/or silicone.

8. The dental or surgical handpiece according to claim 1, wherein
   the push-button is arranged at an upper side of the head piece opposite the tool, the plate-shaped recess essentially being formed at the centre of the push-button.

9. The dental or surgical handpiece according to claim 1, wherein
   the plastic material is polyetheretherketone (PEEK).

10. The dental or surgical handpiece according to claim 1, wherein
    the handle sleeve and the head piece are made of metal.

11. The dental or surgical handpiece according to claim 1, wherein
    the handle sleeve has an angled design.

12. The dental or surgical handpiece according to claim 1, wherein
    a drive motor or a shaft is disposed in the handle sleeve, the handle sleeve further housing a bearing-mounted drive train for transmitting a rotational motion to the tool held at the headpiece.

13. The dental or surgical handpiece according to claim 1, wherein
    the clamping mechanism has a collet for holding a shaft of the tool.

14. The dental or surgical handpiece according to claim 1, wherein the push-button is arranged at an upper side of the head piece opposite the tool, and the plate-shaped recess essentially being formed at a center of the push-button.

15. A head piece for a dental or surgical handpiece,
    the head piece having the purpose to detachably receive a dental tool,
    a clamping mechanism being formed in the head piece for detachably holding the tool, said clamping mechanism having a push-button for actuating the clamping mechanism,
    the push-button consisting of a heat-insulating electrically non-conductive plastic or ceramic material with a plate-shaped recess, and
    an RFID transponder disposed in the plate-shaped recess; the RFID transponder provided for identifying the handpiece wherein the plate-shaped recess is on top of the push-button and the plate-shaped recess opens away from the head piece.

16. The head piece according to claim 15, wherein the push-button is arranged at an upper side of the head piece.

17. The head piece according to claim 15, wherein the RFID transponder is completely disposed in the plate-shaped recess.

18. A dental or surgical handpiece comprising: an elongated handle sleeve, a head piece arranged at the front end of the handle sleeve for detachably receiving a dental tool, a clamping mechanism formed in the head piece for detachably holding the tool, said clamping mechanism having a push-button for actuating the clamping mechanism, the push-button including a heat-insulating electrically non-conductive plastic or ceramic material with a plate-shaped recess, and an RFID transponder provided for identifying the handpiece, the RFID transponder being disposed in the plate-shaped recess of the push-button; wherein the RFID transponder is completely disposed in the plate-shaped recess.

* * * * *